United States Patent
Luo et al.

(10) Patent No.: US 11,974,879 B2
(45) Date of Patent: May 7, 2024

(54) THREE DIMENSIONAL MECHANICAL ULTRASOUND PROBE

(71) Applicant: EDAN INSTRUMENTS, INC., Shenzhen (CN)

(72) Inventors: Hua Luo, Shenzhen (CN); Jianhua Mo, Shenzhen (CN); Bo Ouyang, Shenzhen (CN); Dan Zhou, Shenzhen (CN)

(73) Assignee: EDAN INSTRUMENTS, INC., Shenzhen (CN)

( * ) Notice: Subject to any disclaimer, the term of this patent is extended or adjusted under 35 U.S.C. 154(b) by 784 days.

(21) Appl. No.: 16/541,645

(22) Filed: Aug. 15, 2019

(65) Prior Publication Data

US 2020/0077980 A1 Mar. 12, 2020

(30) Foreign Application Priority Data

Sep. 6, 2018 (CN) .......................... 201811035479.7

(51) Int. Cl.
*A61B 8/00* (2006.01)
(52) U.S. Cl.
CPC .................................. *A61B 8/4461* (2013.01)
(58) Field of Classification Search
None
See application file for complete search history.

(56) References Cited

U.S. PATENT DOCUMENTS

| | | | | |
|---|---|---|---|---|
| 2006/0241368 A1* | 10/2006 | Fichtinger | ................ | A61B 5/06 600/407 |
| 2006/0284086 A1* | 12/2006 | Hasegawa | ............ | G01N 29/265 250/309 |
| 2009/0177088 A1* | 7/2009 | Hasegawa | ............ | A61B 8/4461 600/445 |
| 2013/0150725 A1* | 6/2013 | Choi | ........................ | A61B 8/08 600/472 |
| 2014/0213907 A1* | 7/2014 | Havel | .................. | A61B 8/0891 600/462 |
| 2017/0105702 A1* | 4/2017 | Naka | ...................... | A61B 8/483 |

* cited by examiner

*Primary Examiner* — Shahdeep Mohammed

(57) ABSTRACT

Disclosed is a three dimensional mechanical ultrasound probe, which includes a transducer, a driving motor and a transmission mechanism configured to drive the transducer to reciprocatingly oscillate within a predetermined angle. The transmission mechanism includes a transducer base fixed and connected with the transducer, a face gear arranged on the transducer base, and a cylindrical gear meshed with the face gear. A rotating shaft of the face gear is positioned on the transducer base, and the face gear drives the transducer base to reciprocatingly oscillate. A transmission shaft is arranged on the axis of the cylindrical gear, and the transmission shaft is connected with the driving motor. The three dimensional mechanical ultrasound probe provided by the present application aims at simplifying the internal structure of the three dimensional mechanical ultrasound probe, reducing the internal installation complexity and improving motion stability.

12 Claims, 15 Drawing Sheets

THREE DIMENSIONAL MECHANICAL ULTRASOUND PROBE

TECHNICAL FIELD

The present application relates to the technical field of medical instruments, in particular to a three dimensional mechanical ultrasound probe.

BACKGROUND

The three dimensional (hereinafter 3D) mechanical ultrasound probe is an ultrasound probe used in a 3D ultrasound imaging system, in which a driving motor is served as a driving power source therein. The driving motor takes an internal mechanical transmission device to drive a transducer to oscillate within a certain angle. In the oscillating course of the transducer, the 3D mechanical ultrasound probe can transmit and receive ultrasound just like a traditional ultrasound probe, to continuously scan the tissue of a human body within the oscillating angle to acquire data for 3D imaging. It is not required to slide or oscillate the probe on the human body by doctor.

This kind of probe is of vital importance to provide a transmission mechanism that enables the transducer to oscillate within a certain range. That is, the transmission mechanism converts the rotation of the driving motor in the probe, to the oscillation of the transducer within a certain range. The current 3D mechanical ultrasound probe generally implement the transmission with belt transmission as a first stage transmission, and bevel gear as a second stage. Due to an axial error, a special anti-dislocation structure has to be provided to the bevel gear, which results in a relatively complex internal structure of the probe and a lower installation accuracy of the bevel gear.

SUMMARY

The main objective of the present application is to provide a 3D mechanical ultrasound probe, aiming at simplifying the internal structure of the 3D mechanical ultrasound probe, reducing the internal installation complexity, and improving the transmission stability.

In order to achieve the aforementioned objective, a 3D mechanical ultrasound probe is provided, including: a transducer, a driving motor, and a transmission mechanism configured to drive the transducer to reciprocatingly oscillate within a predetermined angle. The transmission mechanism includes a transducer base fixed and connected with the transducer, a face gear arranged on the transducer base, and a cylindrical gear meshed with the face gear. A rotating shaft of the face gear is positioned on the transducer base, and the face gear drives the transducer base to reciprocatingly oscillate. A transmission shaft is arranged on the axis of the cylindrical gear, and the driving motor drives the transmission shaft to drive the cylindrical gear to rotate.

In one embodiment, an included angle formed between a rotating center line of the face gear and a rotating axis of the transducer base is equal to or larger than 0 degree and smaller than 90 degrees.

In one embodiment, the included angle is equal to 0 degree, and a rotating axis of the cylindrical gear is perpendicular to the rotating center line of the face gear.

In one embodiment, the face gear is spur cylindrical, helical cylindrical, arc cylindrical or herringbone cylindrical.

In one embodiment, the face gear is a spur cylindrical face gear, and the cylindrical gear is a spur cylindrical gear; or the face gear is a helical cylindrical gear, and the cylindrical gear is a helical cylindrical gear In one embodiment, the cylindrical gear is an involute gear.

In one embodiment, the 3D mechanical ultrasound probe further includes a probe base including a base and a side wall extending in a same direction from an end of the base; two ends of the transducer base are rotatably arranged on opposite side walls of the probe base; the 3D mechanical ultrasound probe further includes a reduction gearbox which are arranged at a side of the base away from the transducer base and transmitting a reduced speed of the driving motor to the cylindrical gear.

In one embodiment, the reduction gearbox includes a driving cylindrical gear and a driven cylindrical gear meshed with the driving cylindrical gear; one end of the driving cylindrical gear shaft is rotatably connected to the probe base, and the other end of the driving cylindrical gear shaft passes through the reduction gearbox and connected with an output shaft of the driving motor; the driven cylindrical gear is sleeved on the transmission shaft and is a coaxial gear with the transmission shaft.

In one embodiment, an included angle formed between a rotating center line of the face gear and a rotating axis of the transducer base is equal to 0 degree; a rotating axis of the cylindrical gear is perpendicular to the rotating center line of the face gear; a rotating axis of the driving cylindrical gear is parallel to a rotating axis of the driven cylindrical gear.

In one embodiment, the face gear is spur cylindrical, helical cylindrical, arc cylindrical or herringbone cylindrical.

In one embodiment, the face gear is a spur cylindrical face gear, and the cylindrical gear is a spur cylindrical gear; or the face gear is a helical cylindrical gear, and the cylindrical gear is a helical cylindrical gear.

In the technical solution according to the present application, the internal space of the 3D mechanical ultrasound probe is well reduced by adopting a first stage gear transmission formed by the face gear and the cylindrical gear. The installation structure is simplified, facilitating the probe assembly and installation. A 3D mechanical ultrasound probe is flexibly designed which better conforms with clinical medical ergonomics. In the meanwhile, the transmission stability is increased due to a high contact ratio of face gear transmission. The motion noise is low, and the imaging quality is improved. The working performance is generally improved of the present 3D mechanical ultrasound probe.

BRIEF DESCRIPTION OF THE DRAWINGS

As following, the technical solution in the embodiments of the present application will be described clearly and completely with reference to the drawings in the embodiment of the present application. Obviously, the described embodiment is only a part of the embodiment of the present application, not all of the embodiments. Based on the embodiments in the present application, all other embodiments perceived by those ordinary skills in the art without creative effort should be fallen within the protection scope of the present application.

DESCRIPTION OF REFERENCE NUMERALS

Figure 1:
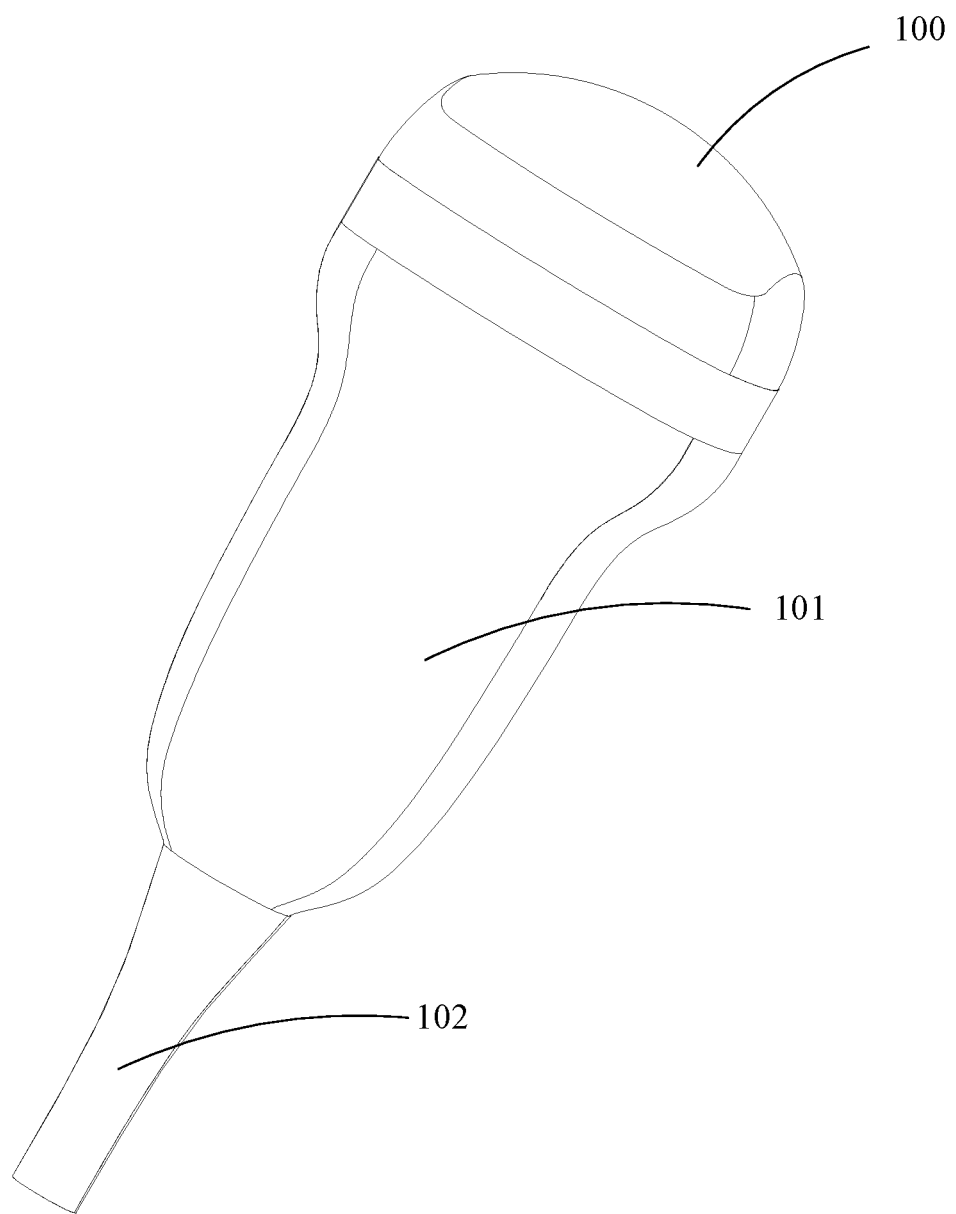
FIG. 1 is a schematic perspective view of a 3D mechanical ultrasound probe of the present application.

| Reference Numeral | Name |
| --- | --- |
| 100 | Acoustic window |
| 101 | Handle housing |
| 102 | Tail sleeve assembly |
| 103 | Sealing liquid |
| 104 | Transducer |
| 105 | Probe base |
| 1051 | Base |
| 1052 | Side wall |
| 106 | Transmission mechanism |
| 107 | Transducer base |
| 108 | Flange bearing |
| 109 | Deep groove ball bearing |
| 110 | Base shaft |
| 111 | Positioning pin |

-continued

| Reference Numeral | Name |
| --- | --- |
| 112 | Face gear |
| 113 | Cylindrical gear |
| 114 | Transmission shaft |
| 115 | Skeleton oil seal |
| 116 | Reduction gearbox |
| 117 | Driving cylindrical gear |
| 118 | Driven cylindrical gear |
| 119 | Driving motor |
| 120 | Coupling |
| 121 | Motor fixing base |
| 122 | Position sensing assembly |
| 123 | Photoelectric element |
| 124 | Photoelectric shutter |
| 125 | Photoelectric sensor support |

The implementation, functional features and advantages of the present application will be further described with reference to the accompanying drawings with the examples.

DETAILED DESCRIPTION OF THE EMBODIMENTS

As following, the technical solution in the examples of the present application will be described clearly and completely with reference to the drawings in the example of the present application. Obviously, the described example is only a part of the example of the present application, not all of the examples. Based on the examples in the present application, all other examples perceived by those ordinary skills in the art without creative effort should be fallen within the protection scope of the present application.

It should be noted that all directional indicators (such as upper, lower, left, right, front, rear, etc.) in the example of the present application are only used to explain the relative positional relationship, movement, etc. between various components under a certain specific posture (as shown in the drawings). If the specific posture changes, the directional indicator will also change accordingly.

In addition, the descriptions related to "first", "second" and the like in the present application are for descriptive objectives only and cannot be understood as indicating or implying its relative importance or implicitly indicating a number of technical features indicated. Thus, features defining "first" and "second" may explicitly or implicitly include at least one of the features. In the description of the present application, the meaning of "plural" is at least two, such as two, three, etc., otherwise specifically defined.

In the present application, the terms "connected" and "fixed" etc. should be understood in a broad sense, otherwise specified and defined. For example, "fixed" can be a fixed connection, a detachable connection, or an forming a part integrally; It can be a mechanical connection or an electrical connection; It can be a direct connection or an indirect connection through an intermediate medium; and it can be the communication between interior of two elements or the interaction between two elements, otherwise specifically defined. For those ordinary skilled in the art, the specific meanings of the aforementioned terms in the present application can be understood according to practical conditions.

In addition, the technical solutions between the various examples can be combined with each other, but it must be based on the realization by ordinary skilled in the art. When the combination of technical solutions is contradictory or cannot be realized, it should be considered that the combination of such technical solutions does not exist and is not within the scope of protection claimed in the present application.

The present application provides a 3D mechanical ultrasound probe.

Figure 2:
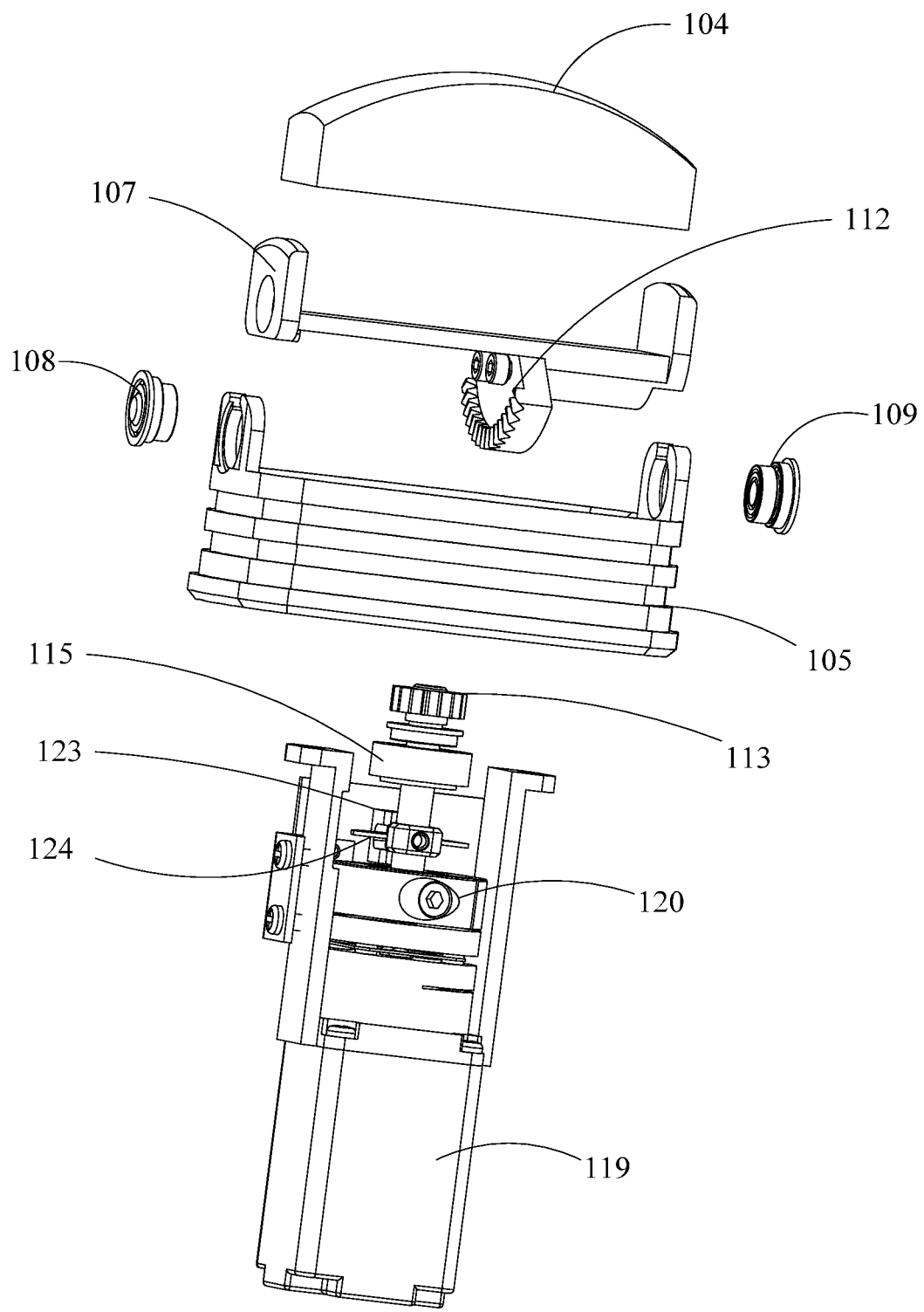
FIG. 2 is an exploded diagram of a part of a 3D mechanical ultrasound probe according to example 1 of the present application.
Figure 3:
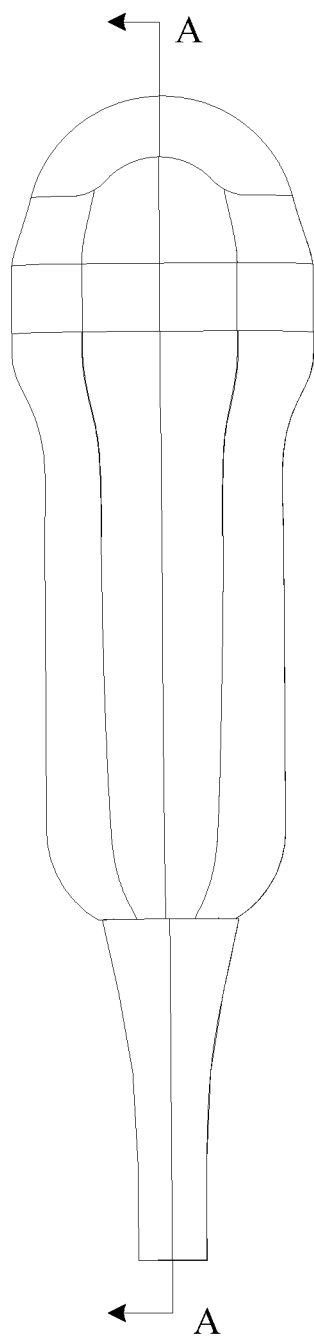
FIG. 3 is a side view of the 3D mechanical ultrasound probe according to the example 1 or example 3 of the present application.
Figure 4:
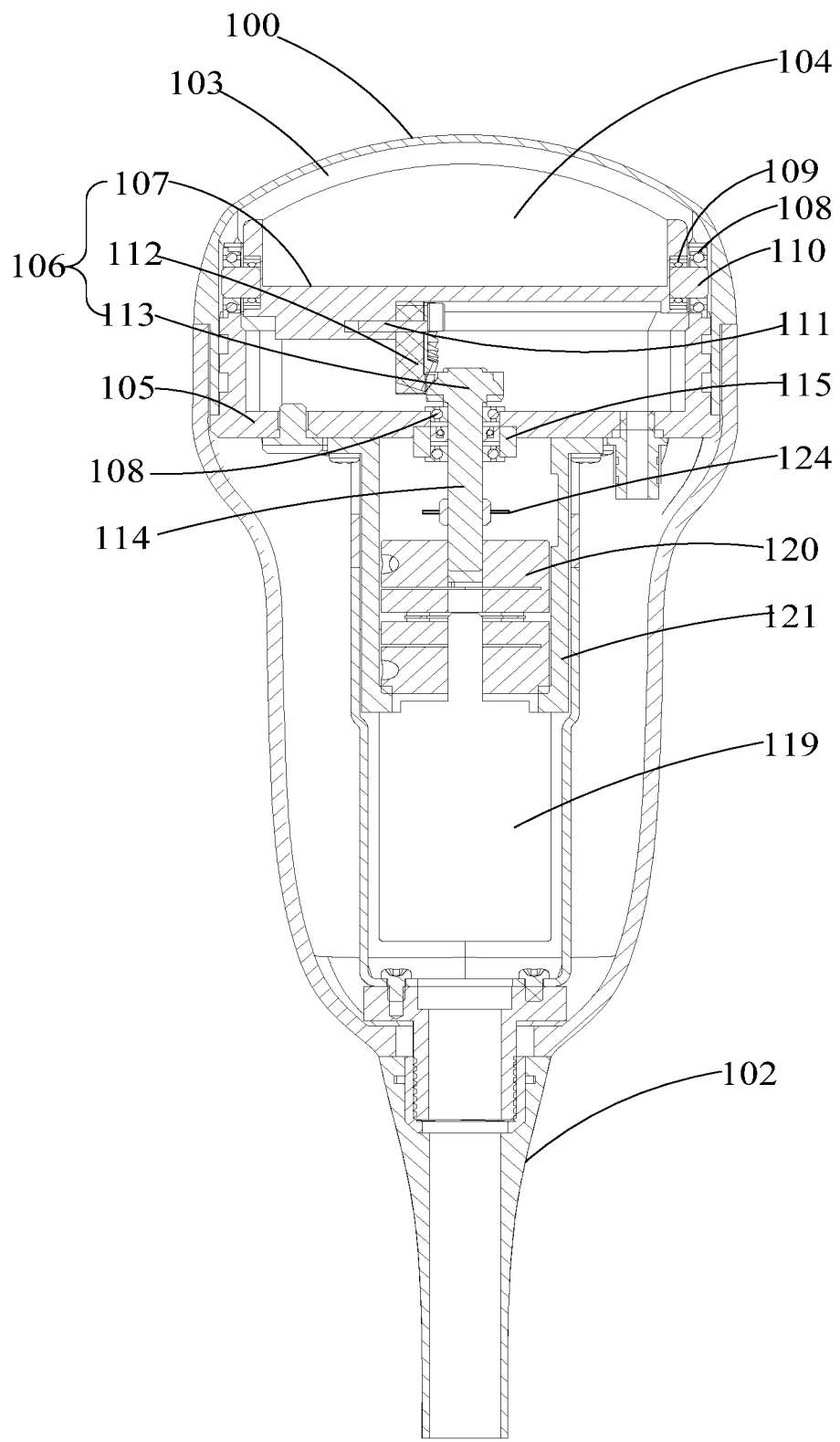
FIG. 4 is a cross-sectional view along line A-A according to the example 1 of a 3D mechanical ultrasound probe of the present application.
Figure 5:
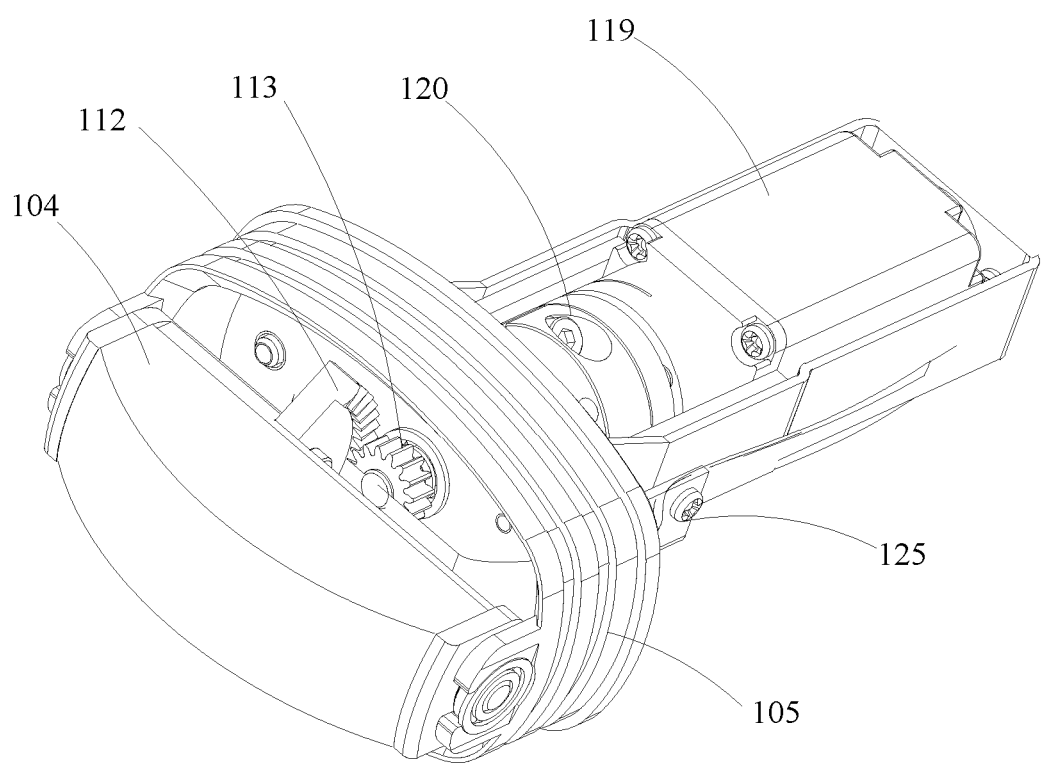
FIG. 5 is a schematic diagram showing an internal structure of a 3D mechanical ultrasound probe according to the example 1 of the present application after a part of the external structure is removed.
Figure 6:
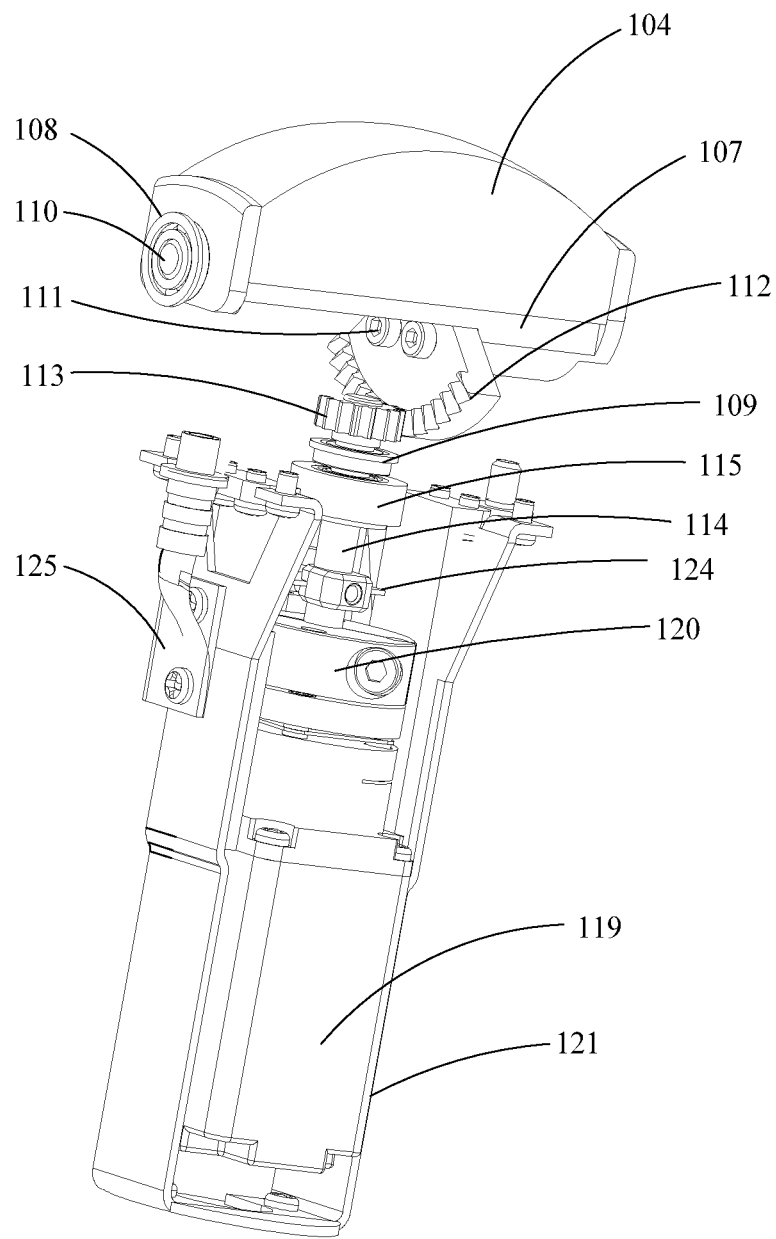
FIG. 6 is a schematic diagram showing an internal structure of a 3D mechanical ultrasound probe after a part of the external structure and the probe base are removed according to the example 1 of the present application.

Referring to FIGS. 2 and 4, in an example of the present application, the 3D mechanical ultrasound probe includes a transducer 104, a driving motor 119, and a transmission mechanism 106 for driving the transducer 104 to reciprocatingly oscillate within a predetermined angle. The transducer 104 is configured to transmit and receive ultrasound signals. The transmission mechanism 106 includes a transducer base 107 fixed and connected with the transducer 104, a face gear 112 arranged on the transducer base 107, a rotating shaft of the face gear 112 positioned on the transducer base 107. The face gear 112 drives the transducer base 107 to reciprocatingly oscillate, and an included angle formed between a rotating center line of the face gear and a rotating axis of the transducer base is equal to or larger than 0 degree and smaller than 90 degree. A cylindrical gear 113 is meshed with the face gear 112, and a transmission shaft 114 is arranged on the axis of the cylindrical gear 113. The transmission shaft 114 drives the cylindrical gear 113 to rotate under the driving motor 119.

In the technical solution according to the present application, the internal space of the 3D mechanical ultrasound probe is well reduced by adopting a first stage gear transmission forming by the face gear 112 and the cylindrical gear 113. The installation structure is simplified, facilitating the probe assembly and installation. A 3D mechanical ultrasound probe is flexibly designed which better conforms with clinical medical ergonomics. In the meanwhile, the transmission stability is increased due to a high contact ratio of face gear 112 transmission. The motion noise is low, and the imaging quality is improved. The working performance is generally improved of the present 3D mechanical ultrasound probe.

Example 1

Please refer to FIGS. 1 to 8. The 3D mechanical ultrasound probe according to this example has a transmission mechanism with the first-stage face gear. The 3D mechanical ultrasound probe includes an acoustic window 100, a handle shell 101 and a tail sleeve assembly 102 which are matched and connected to form an external shape, and other structures are all positioned inside the probe.

Specifically, the 3D mechanical ultrasound probe further includes a probe base 105, the transducer 104 is fixedly arranged on the transducer base 107, the transducer base 107 are arranged on the probe base 105 at two ends through the flange bearing 108, the deep groove ball bearing 109, and the base rotating shaft 110. The transducer base 107 can reciprocatingly oscillate relative, to the probe base 105 around the base rotating shafts 110 at two sides of the transducer base 107 within a certain angle. The probe base 105 and the acoustic window 100 are sealed by epoxy glue, forming a sealed space which is completely filled with sealing liquid 103 with an acoustic propagation. The transducer 104 can reciprocatingly oscillate in the sealed space formed by the probe base 105 and the acoustic window 100, and ultrasound signals can be emitted and received through the sealing liquid 103. The cylindrical gear 113 is arranged and fixed on the probe base 105 through a flange bearing 108 and a skeleton oil seal 115, and can freely rotate relative to the probe base 105. The face gear 112 meshed with and driven by the cylindrical gear 113 is arranged on the transducer base 107 through screws (not shown) and the positioning pin 111. The included angle formed between the rotating center line of the face gear 112 and the rotating axis of the transducer base 107 is equal to 0 degree. The rotating axis of the cylindrical gear 113 is perpendicular to the rotating center line of the face gear 112, which forms a first-stage face gear transmission.

Specifically, the shaft end of the cylindrical gear 113 is abutted to the output shaft of the driving motor 119 through a coupling 120. The coupling 120 may be an elastic coupling or a rigid coupling. In the case of an elastic coupling, the shaft aligning requirement of the driving motor 119 and the cylindrical gear 113 can be reduced; the axial, radial and angular deviations be compensated, and vibration generated in the operation of the driving motor 119 can be buffered. In the case of a rigid coupling, it is required to ensure the shaft alignment between the driving motor 119 and the cylindrical gear 113 with no buffer of vibration generated from the driving motor, which in return can transmit a larger torque. The driving motor 119 is fixed and connected with the motor fixing base 121 through screws, and the motor fixing base 121 is fixed and connected with the probe base 105 through screws.

Figure 7:
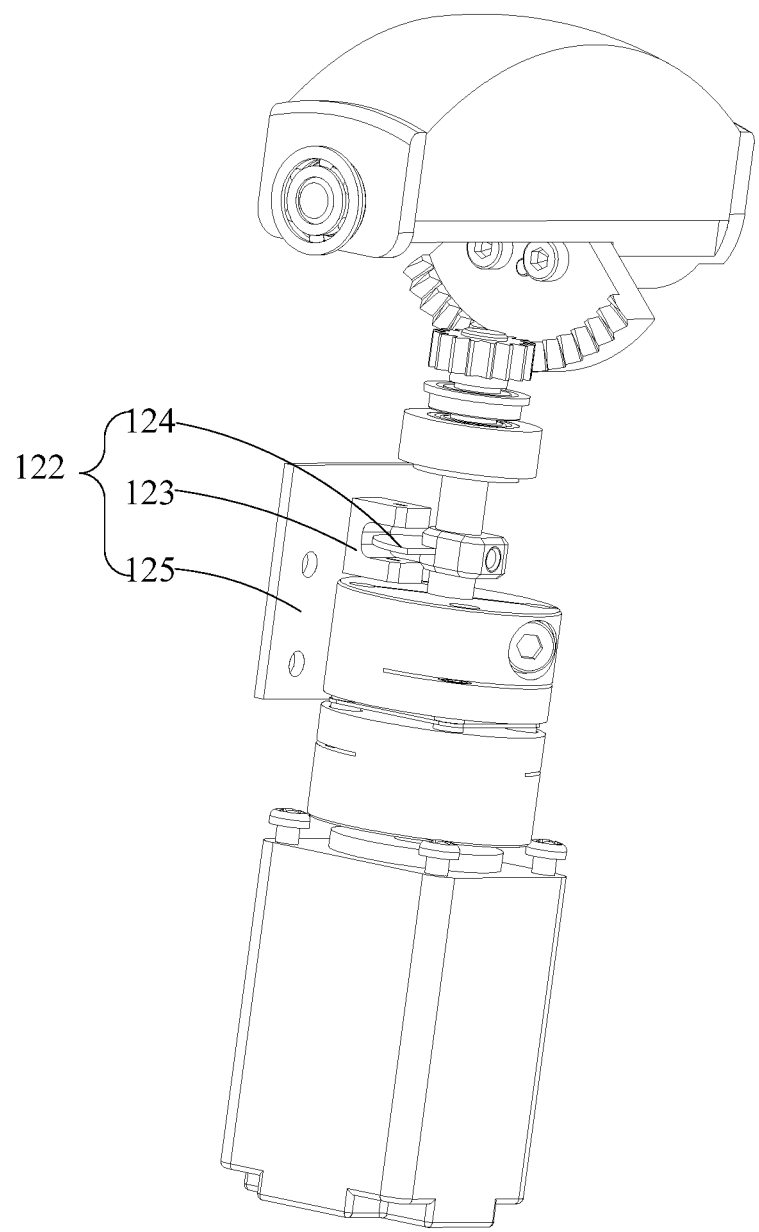
FIG. 7 is a schematic view of the position structure of a position sensor assembly of an 3D mechanical ultrasound probe according to the example 1 of the present application.
Figure 8:
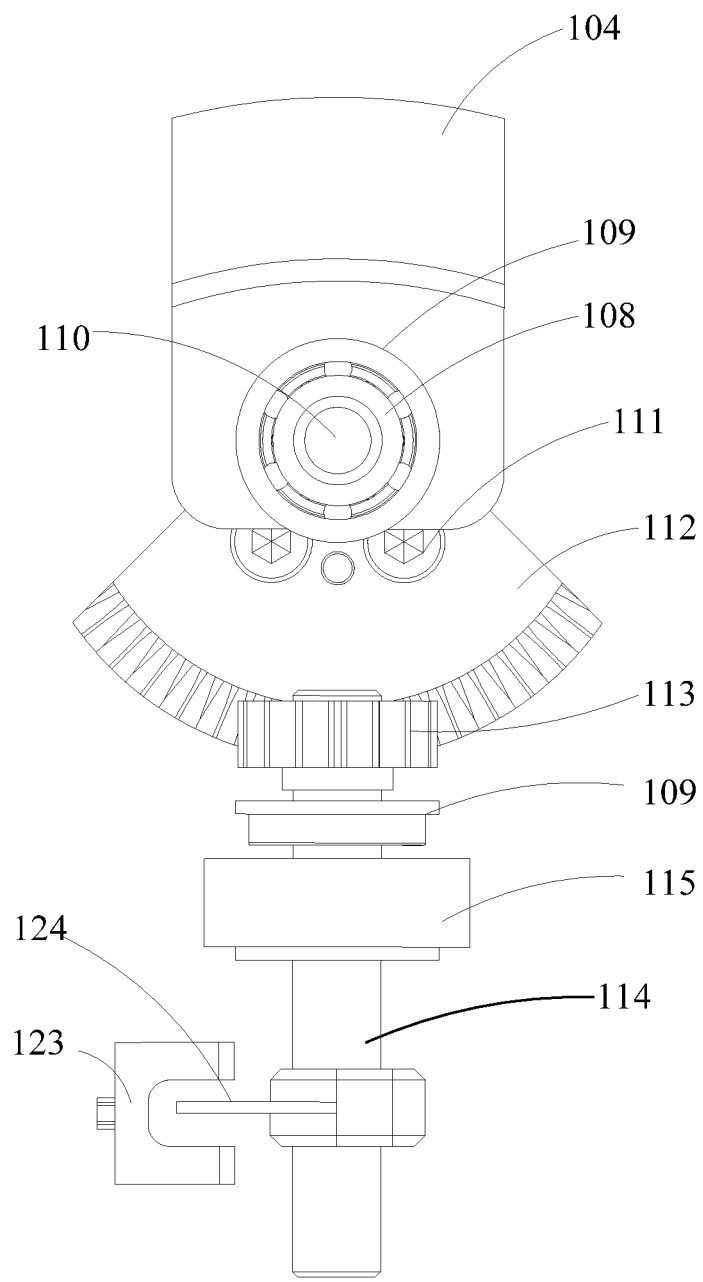
FIG. 8 is a side view of a transmission mechanism according to the example 1 of a 3D mechanical ultrasound probe of the present application.

Specifically, please refer back to the detailed FIGS. 7 and 8. The 3D mechanical ultrasound probe further includes a position sensing assembly 122, which includes a photoelectric element 123, a photoelectric shutter 124 and a photoelectric sensor support 125. In which, the photoelectric element 123 is arranged on and connected to the photoelectric sensor support 125 through screws, and the photoelectric shutter 124 is fixed and arranged at the middle part of the rear end of the shaft of the cylindrical gear 113 through a set screw, which can synchronously rotate with the cylindrical gear 113, and pass through the groove defined by the photoelectric element 123. The photoelectric element 123 switches on and off the circuit feedback signal of the photoelectric shutter 124 to the driver of the driving motor 119, and then sends an instruction to the driving motor 119 to change direction, thus realizing the reciprocal movement of the probe.

In specific operation, when the driving motor 119 is powered on, the output shaft of the driving motor 119 rotates to drive the cylindrical gear 113 to rotate through the coupling 120, and the face gear 112 rotates through the orthogonal face gear transmission. Since the face gear 112 is fixedly installed on the transducer base 107, the motion is transmitted to the transducer base 107, which in turn drives the transducer 104 installed on the transducer base 107 to move. When the signal transmitted from the driver of the driving motor to the driving motor 119 is a continuous periodic signal, the transducer 104 can reciprocatingly oscillate around the center of the rotating shaft 110 of the transducer base 107 within a certain range through the transmission of the face gear 112 and the cylindrical gear 113. Thus, the 3D mechanical ultrasound probe can image human tissues at each angle of reciprocation without requiring the doctor sliding or reciprocating the probe on the surface of the human body.

Specifically, in this example, the face gear 112 may be a complete face gear or an incomplete face gear. If the face gear 112 is an incomplete face gear, it can be directly fixed on the side of the transducer base 107 facing away from the transducer 104; if the face gear 112 is a complete face gear, it can be arranged at either end of the transducer base 107 and coaxially arranged with the transducer base 107, or it can be arranged on the side of the transducer base 107 facing away from the transducer 104 through an L-shaped support.

Compared with the general bevel gear transmission, the face gear 112 has a larger contact ratio which can reach more than two. A large contact ratio is vital to improve the bearing capacity and to increase transmission stability, further improving movement stability of the mechanical probe. Thus, better and more stable data can be acquired and the imaging quality improved. In the meanwhile, the point-contact of face gear 112 transmission, will secure a fixed ratio transmission theoretically, while a point-contact bevel gear transmission can generally not guarantee a fixed ratio transmission in principle, and its transmission ratio fluctuates within a certain range. Therefore, transmission by the face gear 112 has relative small vibration and smaller noise, thus reducing vibration and noise while the 3D mechanical ultrasound probe is operating.

Specifically, in order to simplify the internal structure of the 3D mechanical ultrasound probe and reduce the volume thereof, a complete face gear can be cut into incomplete face gear according to the specific requirements of product design. As such, the first-stage face gear transmission and the simplified internal structure of the 3D mechanical ultrasound probe can both be realized, and the volume thereof can be reduced.

Specifically, the cylindrical gear 113 includes, but is not limited to, a spur cylindrical gear and an involute gear. When the cylindrical gear 113 is an involute cylindrical gear, the error generated by its axial movement hardly affects the transmission performance. However, in an ordinary bevel gear transmission, the cone tops of the bevel gears must coincide, otherwise the axial error will bring serious off-loading. As such, a special anti-misalignment structure is necessary in some important bevel gear transmission. Therefore, a 3D mechanical ultrasound probe of the present application, which adopts a face gear transmission, may reduce the installation precision, facilitating the installation. Further, according to the nature of involute, the common normal of the meshing gears is the same, and will remain at different instances, which is extremely beneficial to power transmission and further improvement of the power conversion efficiency regarding the driving motor 119. When the cylindrical gear 113 is a spur cylindrical gear, there is no axial force on the cylindrical gear 113, which may relieve the support and reduce the weight as well as the internal space of the 3D mechanical ultrasound probe correspondingly. The 3D mechanical ultrasound probe can be designed more flexibly in conformity to clinical medical ergonomics.

Specifically, the cylindrical gear 113 and the face gear 112 can be plastic or metal. The cylindrical gear 113 is preferably metal, and the face gear 112 plastic. This gear transmission formed by the metal cylindrical gear and the plastic face gear requires lower transmission precision than common bevel gears in terms of structural installation. No axial acting force exists, which is stable in transmission, and easy in installation. In the meanwhile, due to the self-lubrication of the plastic gear itself, the wear of the tooth surface can be reduced, and the working life be prolonged. Further, the noise during the transmission can be reduced compared to the general metal gear pair.

Example 2

Figure 9:
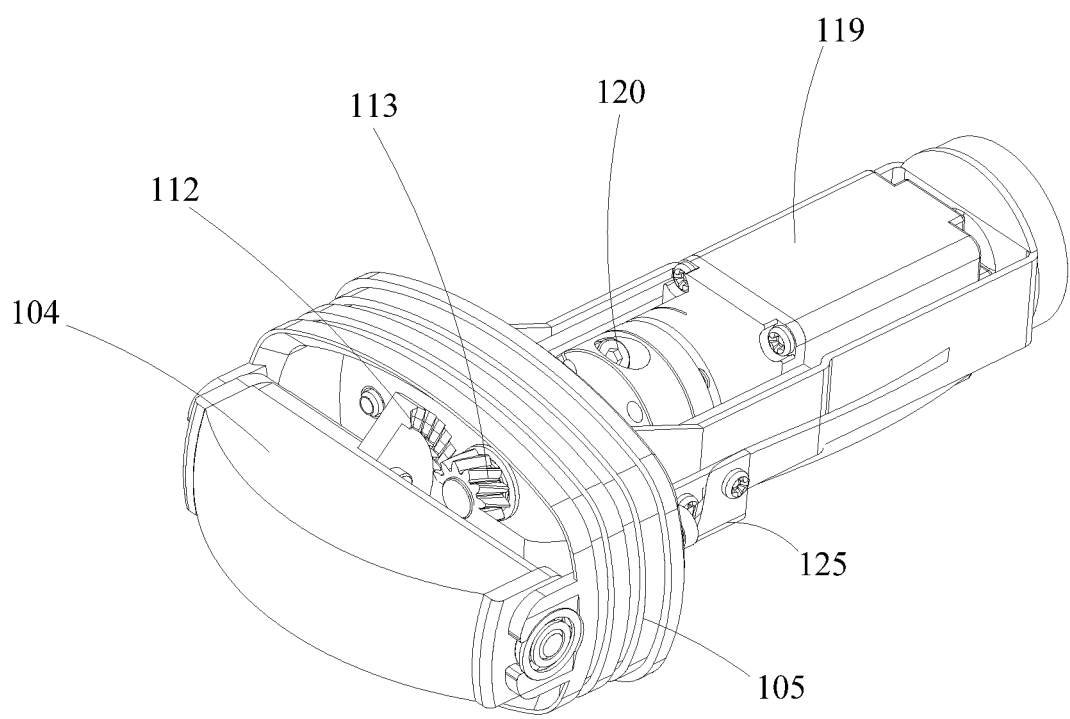
FIG. 9 is a schematic diagram showing an internal structure of a 3D mechanical ultrasound probe according to example 2 of the present application after a part of the external structure is removed.
Figure 10:
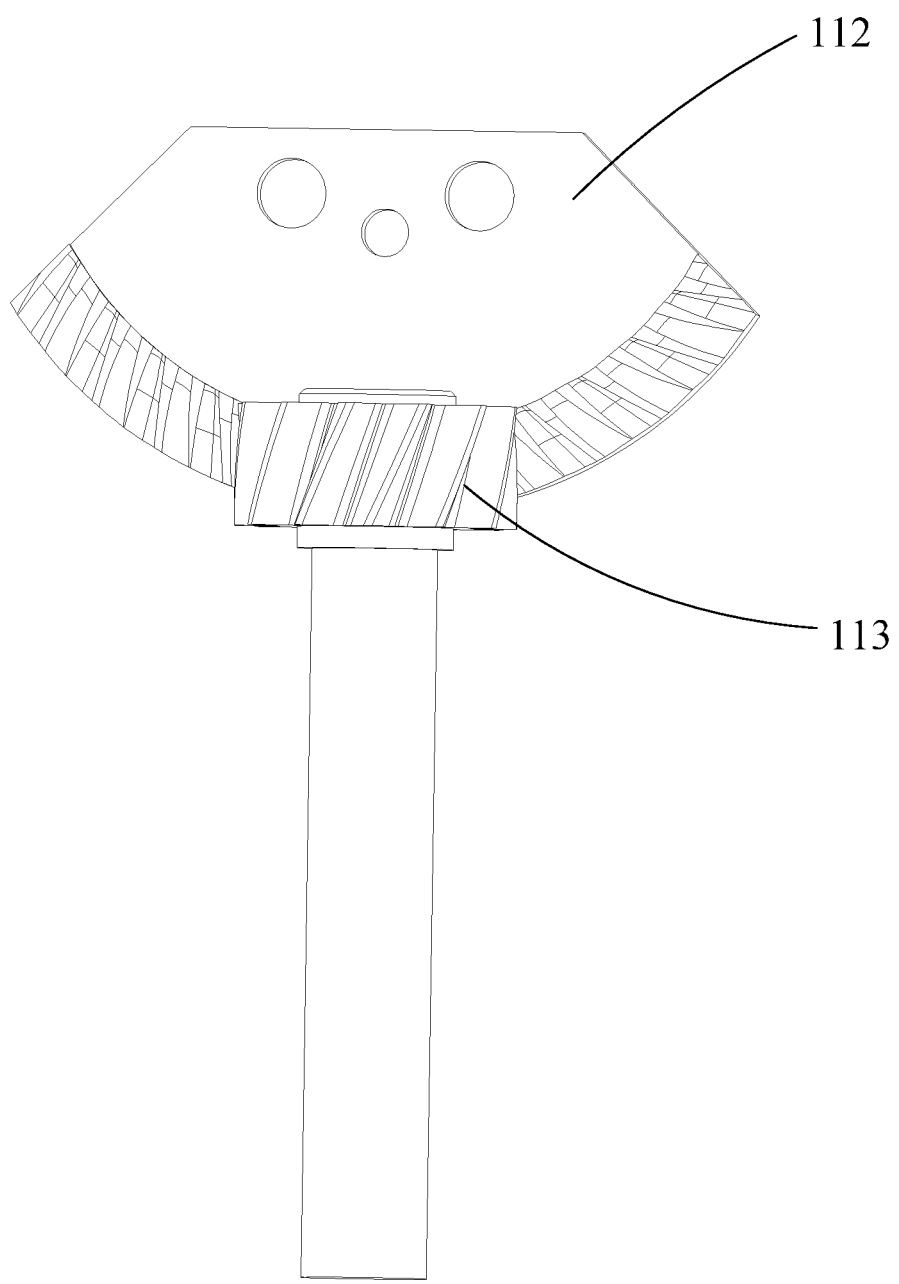
FIG. 10 is a structural schematic diagram of a face gear and a cylindrical gear according to the example 2 of the 3D mechanical ultrasound probe of the present application.
Figure 11:
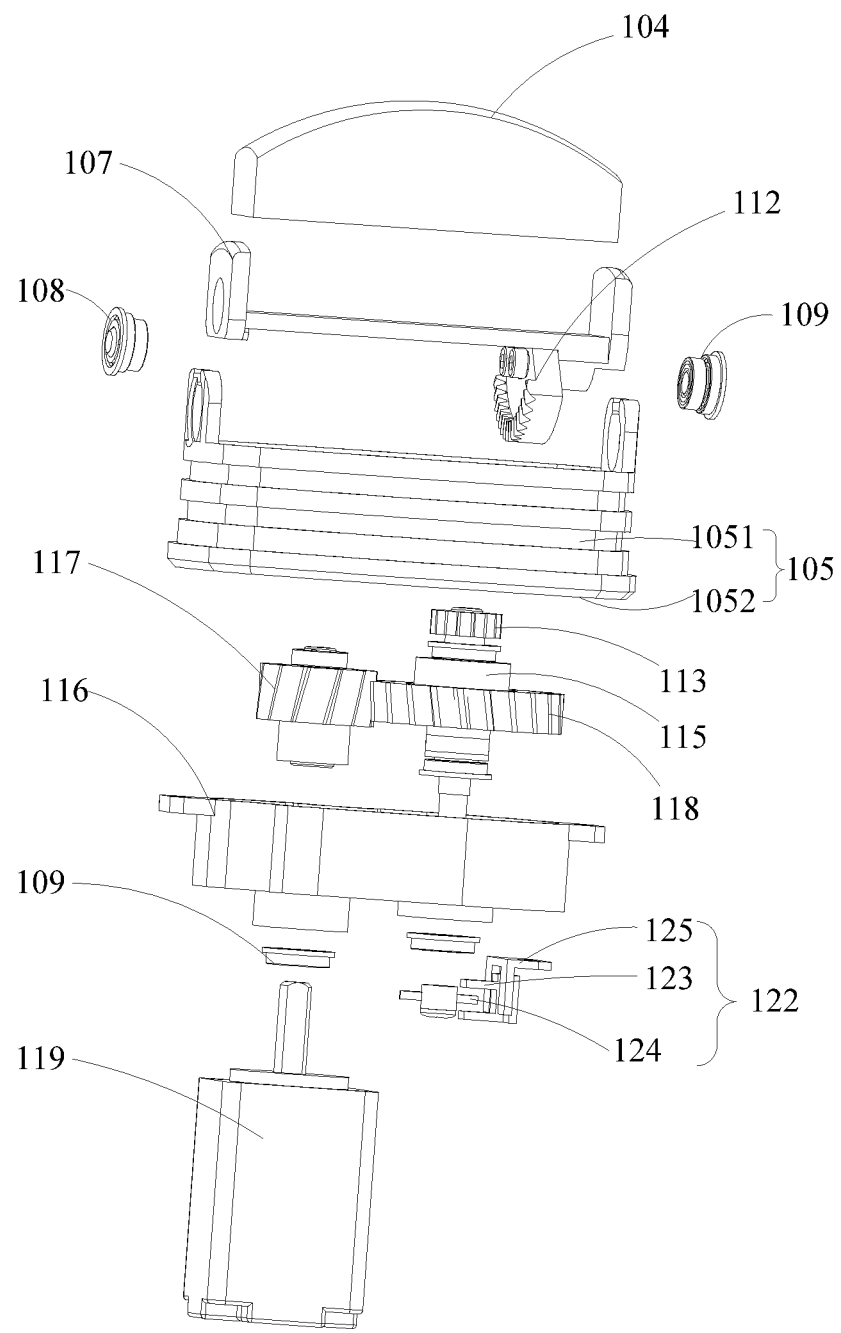
FIG. 11 is an exploded diagram of a part of a 3D mechanical ultrasound probe according to example 3 of the present application.
Figure 12:
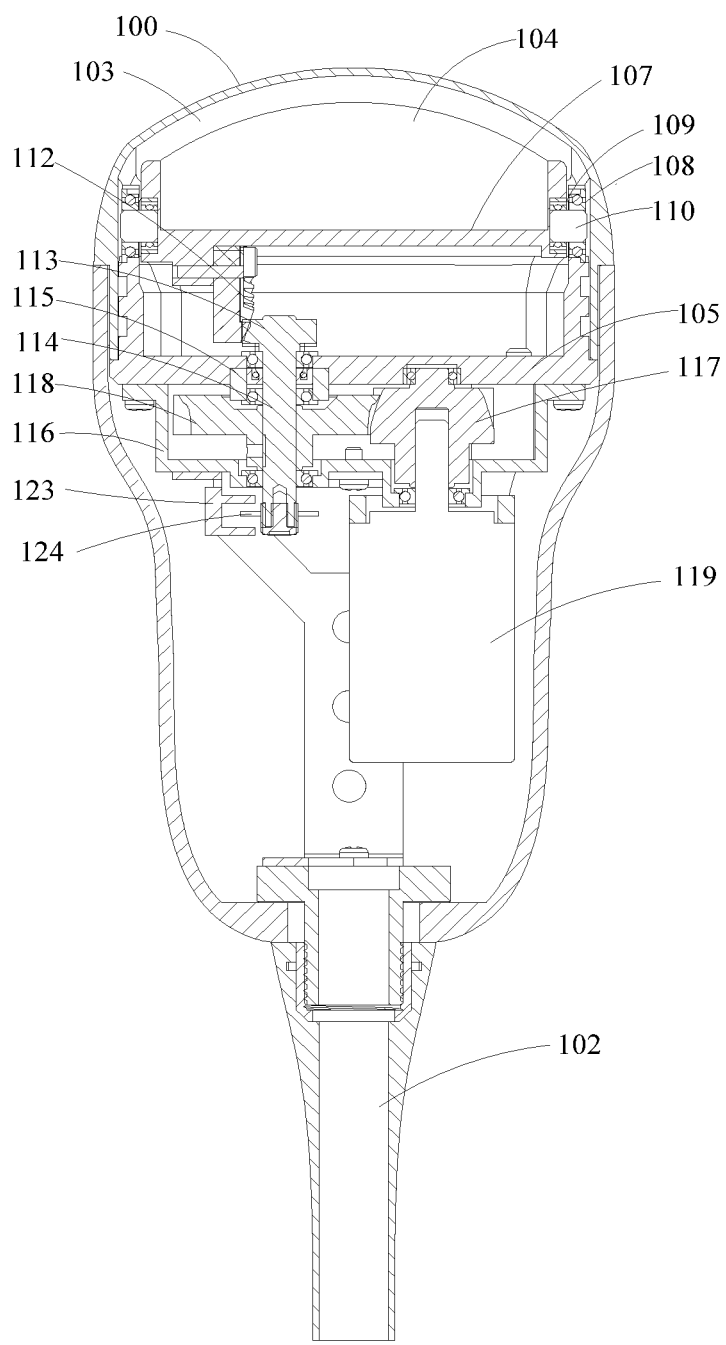
FIG. 12 is a cross-sectional view along line A-A according to the example 3 of a 3D mechanical ultrasound probe of the present application.
Figure 13:
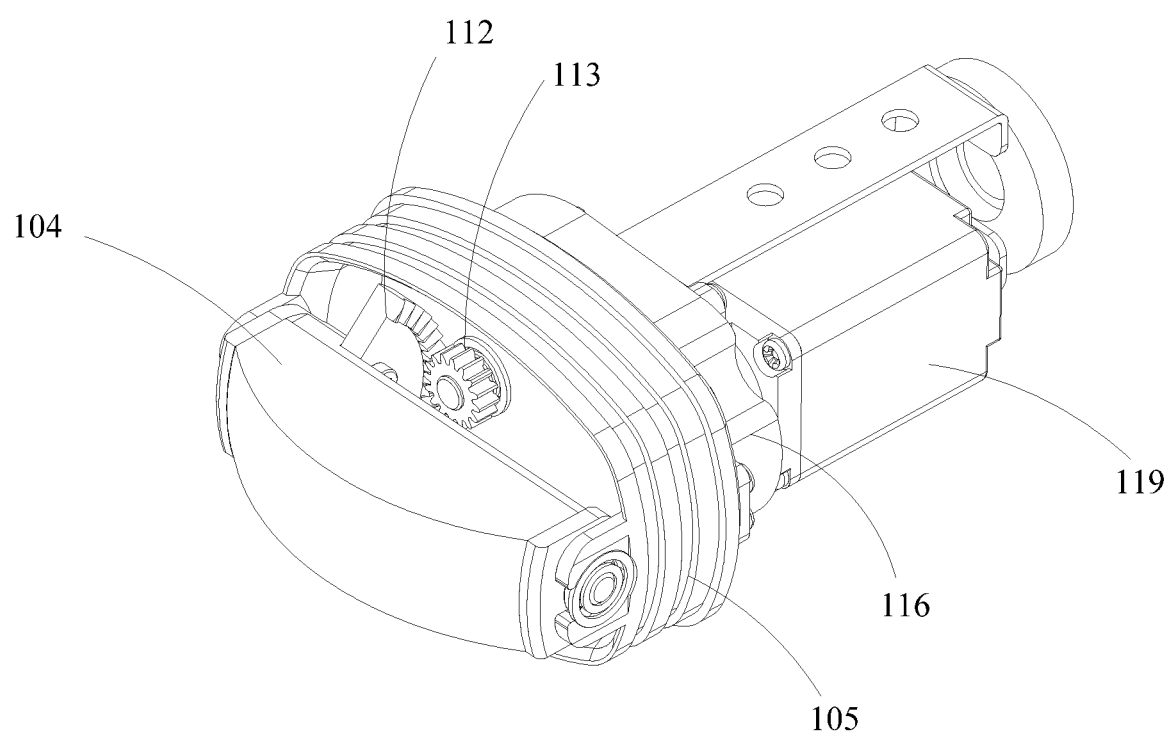
FIG. 13 is a schematic diagram showing an internal structure of a 3D mechanical ultrasound probe according to the example 3 of the present application after a part of the external structure is removed.
Figure 14:
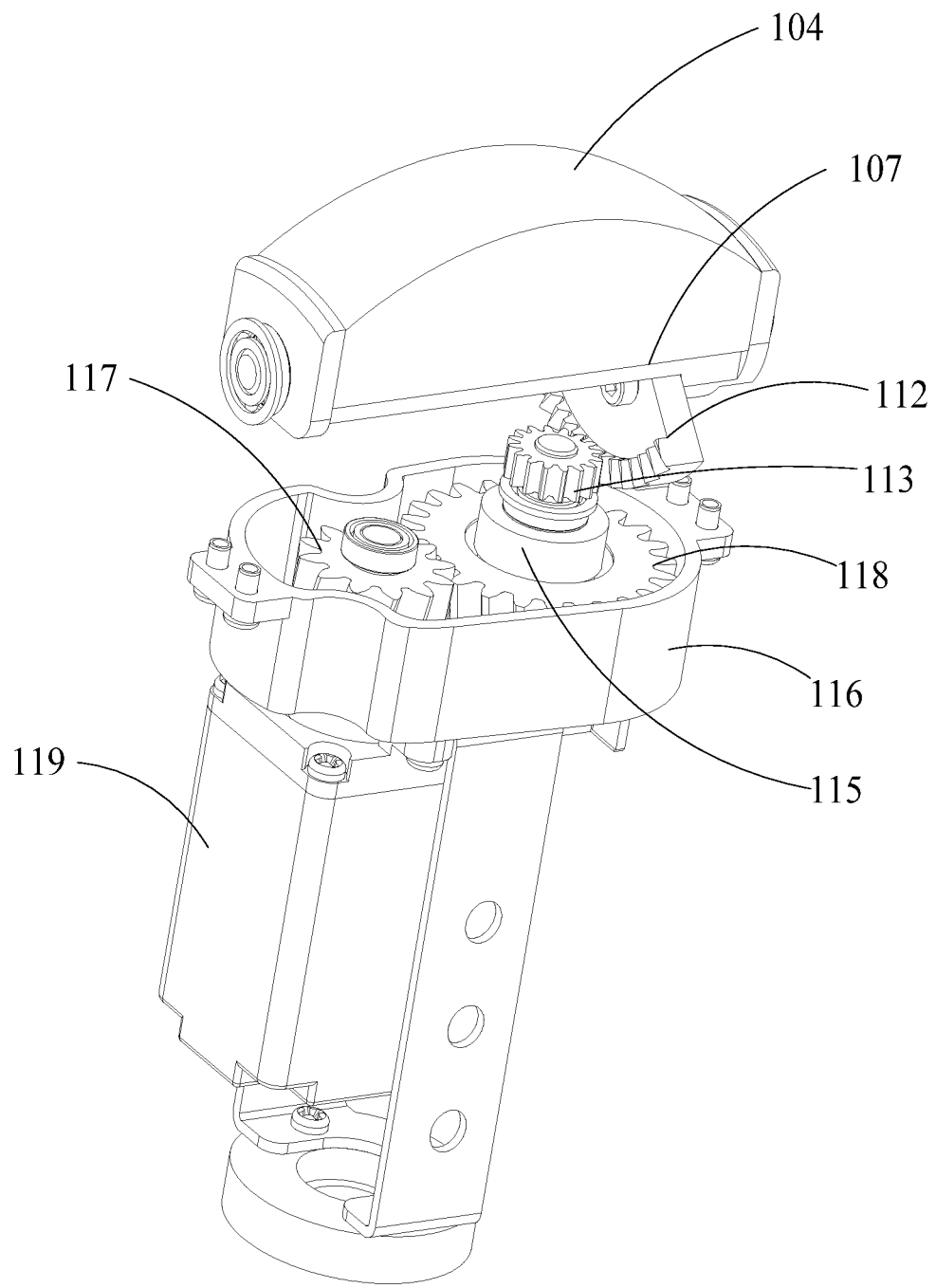
FIG. 14 is a schematic diagram showing an internal structure of a 3D mechanical ultrasound probe after a part of the external structure and the probe base are removed according to the example 3 of the present application.

FIGS. 9 and 10 are referred to, in which the second example of the present application is basically identical to the first aforementioned, except that: the tooth profile of the cylindrical gear 113 and the face gear 112 meshed therewith are helical, that is, the cylindrical gear 113 is helical cylindrical gear and the face gear 112 is helical cylindrical face gear. In the process of helical cylindrical gear transmission, the gear teeth mesh and exit gradually, so the transmission is stable with a small noise and an excellent meshing performance. Further, the contact ratio is large, stabling the transmission and reducing the load each pair of gear teeth has to be borne. The bearing capacity is thus improved. It can be understood that the tooth profile of the cylindrical gear 113 and the face gear 112 meshed therewith is not limited to spur or helical, but may also be other tooth profiles, such as arc-shaped, herringbone, etc.

Example 3

Referring to FIGS. 11 to 14, a two-stage transmission mechanism is provided in the 3D mechanical ultrasound probe of this example, in which the face gear transmission is at the second stage.

Specifically, the transducer 104 is fixedly arranged on the transducer base 107, the transducer base 107 are arranged on the probe base 105 at two ends through the flange bearing 108, the deep groove ball bearing 109, and the base rotating shaft 110. The transducer base 107 can reciprocatingly oscillate relative to the probe base 105 around the base rotating shafts 110 at two sides of, the transducer base 107 within a certain angle. The probe base 105 and the acoustic window 100 are sealed by epoxy glue, forming a sealed space which is completely filled with sealing liquid 103 with an acoustic propagation. The transducer 104 can reciprocatingly oscillate in the sealed space formed by the probe base 105 and the acoustic window 100, and ultrasound signals can be emitted and received through the sealing liquid 103. The cylindrical gear 113 is arranged and fixed on the probe base 10 through a flange bearing 108 and a skeleton oil seal 115, and can freely rotate relative to the probe base 105. The face gear 112 meshed with and driven by the cylindrical gear 113 is arranged on the transducer base 107 through screws and the positioning pin 111. The included angle formed between the rotating center line of the face gear 112 and the rotating axis of the transducer base 107 is equal to 0 degree. The rotating axis of the cylindrical gear 113 is perpendicular to the rotating center line of the face gear 112, which forms a second-stage face gear transmission.

Specifically, the probe base 105 includes a base 1051 and a side wall 1052 extending in a same direction from an end of the base 1051; two ends of the transducer base 107 are rotatably arranged on opposite side walls 1052 of the probe base 105; the 3D mechanical ultrasound probe further comprises a reduction gearbox 116, the reduction gearbox 116 being arranged at a side of the base facing away from the transducer base 107 and transmitting a reduced speed of the driving motor 119 to the cylindrical gear 113. The reduction gearbox 116 includes a driving cylindrical gear 117 and a driven cylindrical gear 118 meshed with the driving cylindrical gear 117. Deep groove ball bearings 109 are respectively provided at two ends of the shaft of the driving cylindrical gear 117. The deep groove ball bearings 109 are fixed and arranged on the probe base 105 and the reduction gearbox 116. The shaft of the driving cylindrical gear 117 is penetrated through the reduction gearbox 116 at one end connected with the reduction gearbox 116, and is connected with the output shaft of the driving motor 119. The driving cylindrical gear 117 can freely rotate relative to the probe base 105 and the reduction gearbox 116. The driven cylindrical gear 118 meshed with the driving cylindrical gear 117 is fixedly arranged on the transmission shaft of the cylindrical gear 113 through screws and can move synchronously with the cylindrical gear 113. The rotating shaft of the driving cylindrical gear 117 is parallel to that of the driven cylindrical gear 118, forming the first-stage transmission.

Specifically, the reduction transmission mechanism in the reduction gearbox 116 is not limited to gear transmission, but can be belt transmission or other forms performing the reduction transmission. The driving motor 119 is fixed and connected with the motor fixing base 121 through screws, and the motor fixing base 121 is fixed and connected with the reduction gearbox 116 through screws.

Specifically, the 3D mechanical ultrasound probe further includes a position sensing assembly 122, which includes a photoelectric element 123, a photoelectric shutter 124 and a photoelectric sensor support 125. In which, the photoelectric element 123 is arranged on and connected to the photoelectric sensor support 125 through screws. And the photoelectric sensor support 125 is arranged at the gearbox 116. The photoelectric shutter 124 is fixed and arranged at the rear end of the shaft of the cylindrical gear 113 through pan head screw, which can synchronously rotate with the cylindrical gear 113, and pass through the groove defined by the photoelectric element 123. The photoelectric element 123 switches on and off the circuit feedback signal of the photoelectric shutter 124 to the driver of the driving motor 119, and then sends an instruction to the driving motor 119 to change direction, thus realizing the reciprocal movement of the probe.

Specifically, when the driving motor 119 is powered, the output shaft of the driving motor 119 rotates, driving the driving cylindrical gear 117 to rotate. The motion is transmitted to the cylindrical gear 113 through the meshing transmission of the first stage gear. The face gear 112 rotates through the transmission of the second-stage orthogonal face gear. Since the face gear 112 is fixed and arranged on the transducer base 107, the motion is transmitted to the transducer base 107, which in turn drives the transducer 104 installed on the transducer base 107 to move. When the signal transmitted from the driver of the driving motor to the driving motor 119 is a continuous periodic signal, the transducer 104 can reciprocatingly oscillate around the center of the rotating shaft 110 of the transducer base 107 within a certain range through the transmission of the face gear 112 and the cylindrical gear 113. Thus, the 3D mechanical ultrasound probe can image human tissues at each angle of reciprocation without requiring the doctor sliding or reciprocating the probe on the surface of the human body.

Specifically, the driving cylindrical gear 117, the driven cylindrical gear 118, the cylindrical gear 113, and the face gear 112 can be plastic or metal. The driving cylindrical gear 117 is preferably metal, and the driven cylindrical gear 118 preferably plastic; the cylindrical gear 113 is preferably metal, and the face gear 112 preferably plastic. The gear pair, due to the self-lubrication of the plastic gear itself, the wear of the tooth surface can be reduced, and the working life be prolonged. Further, the noise during the transmission can be reduced compared to the general metal gear pair.

Example 4

Figure 15:
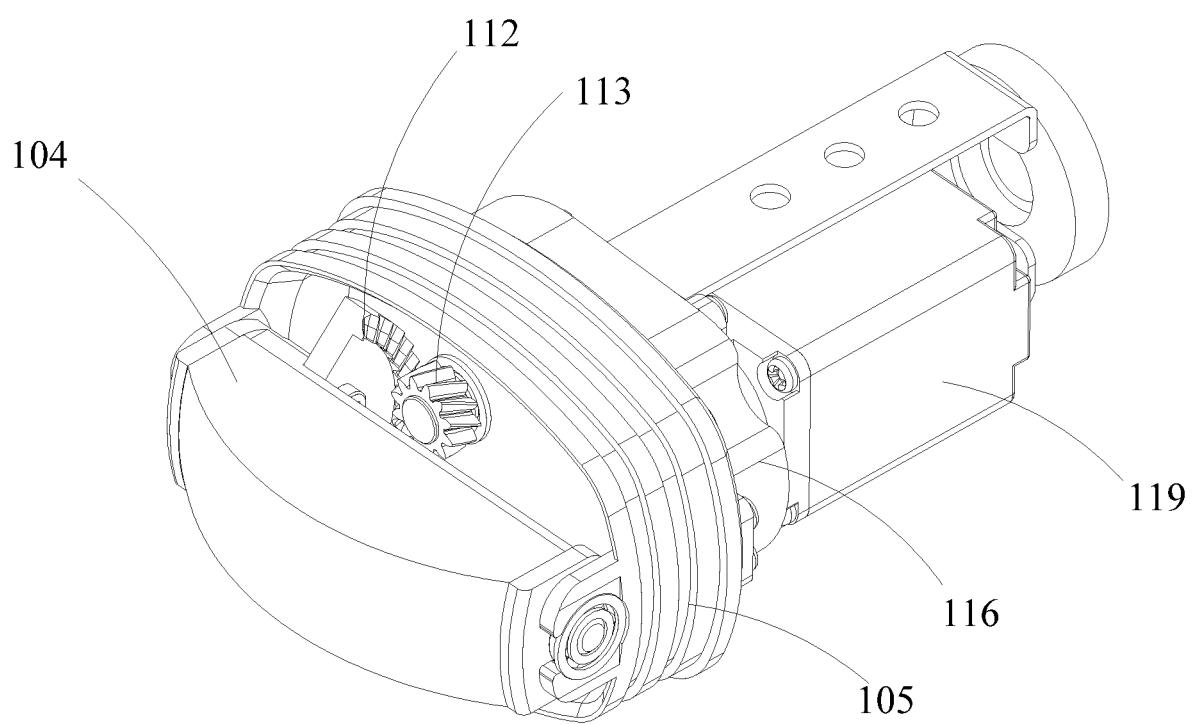
FIG. 15 is a schematic diagram showing an internal structure of a 3D mechanical ultrasound probe according to example 4 of the present application after a part of the external structure is removed.

FIG. 15 is referred to, in which the fourth example of the present application is basically identical to the third one aforementioned, except that: the tooth profile of the cylindrical gear 113 and the face gear 112 meshed therewith are helical, that is, the cylindrical gear 113 is helical cylindrical gear and the face gear 112 is helical cylindrical face gear. In the process of helical cylindrical gear transmission, the gear teeth mesh and exit gradually, so the transmission is stable with a small noise and an excellent meshing performance.

Further, the contact ratio is large, stabling the transmission and reducing the load each pair of gear teeth has to be borne. The bearing capacity is thus improved. It can be understood that the tooth profile of the cylindrical gear 113 and the face gear 112 meshed therewith is not limited to spur or helical, but may also be other tooth profiles, such as arc-shaped, herringbone, etc.

It can be understood that in another example of the present application, the included angle formed between the rotating center line of the face gear 112 and the rotating axis of the transducer base 107 is equal to or greater than 0 degree to less than 90 degrees. Taking 45 degrees as an example, the included angle formed between the rotational center line of the face gear 112 and the rotational axis of the transducer base 107 is 45 degrees, and the rotational axis of the cylindrical gear 113 is perpendicular to the rotational center line of the face gear 112, so that the included angle formed between the rotating axis of the cylindrical gear 113 and the rotating axis of the transducer base 107 is 45 degrees. As such, the handle housing 101, the tail sleeve assembly 102, and some of the internal structures are all inclined, so that a user can handhold the 3D mechanical ultrasound probe with the probe horizontally rather than vertically, which is convenient to use.

The above is only the preferred example of the present application and is not therefore limiting the scope of the present application. Any equivalent structure or process change made by using the contents of the present specification and drawings, or directly or indirectly applied in other related technical fields, shall be included in the protection scope of the present application.

What is claimed is:

1. A three dimensional mechanical ultrasound probe, comprising:
a transducer, a driving motor, and a transmission mechanism configured to drive the transducer to reciprocatingly oscillate within a predetermined angle; wherein
the transmission mechanism comprises a transducer base fixedly connected with the transducer, a face gear arranged on the transducer base, a cylindrical gear meshed with the face gear, and a position detection sensor configured to send an instruction to drive the driving motor to change oscillation directions; wherein
a rotating shaft of the face gear is positioned on the transducer base;
the face gear drives the transducer base to reciprocatingly oscillate;
a transmission shaft is arranged on an axis of the cylindrical gear; and
the driving motor drives the transmission shaft to drive the cylindrical gear to rotate;
the transducer base oscillates around the rotating shaft of the face gear,
wherein a rotating axis of the transmission shaft coincides with the axis of the cylindrical gear, a rotating axis of the face gear is perpendicular to the axis of the cylindrical gear, the position detection sensor is connected between the driving motor and the transmission shaft, and the position detection sensor is disposed at the end of the transmission shaft near the driving motor;
wherein the three dimensional mechanical ultrasound probe further comprises a reduction gearbox connected to a portion of the transmission shaft away from the face gear and is configured to transmit a reduced speed of the driving motor to the cylindrical gear;

the reduction gearbox comprises a driving cylindrical gear and a driven cylindrical gear meshed with the driving cylindrical gear, a driving cylindrical gear shaft of the driving cylindrical gear penetrates through the reduction gearbox and is connected with an output shaft of the driving motor, the driven cylindrical gear is sleeved on the transmission shaft and is a coaxial gear with the transmission shaft; and the cylindrical gear and the driven cylindrical gear are disposed on a same side on the transmission shaft with respect to the position detection sensor.

2. The three dimensional mechanical ultrasound probe of claim 1, wherein the face gear is directly arranged on the transducer base; and the rotating shaft of the face gear is directly positioned on the transducer base.

3. The three dimensional mechanical ultrasound probe of claim 1, wherein an included angle formed between a rotating center line of the face gear and a rotating axis of the transducer base is equal to or greater than 0 degree and smaller than 90 degrees.

4. The three dimensional mechanical ultrasound probe of claim 3, wherein the included angle is equal to 0 degree, and a rotating axis of the cylindrical gear is perpendicular to the rotating center line of the face gear.

5. The three dimensional mechanical ultrasound probe of claim 1, wherein the face gear is spur cylindrical, helical cylindrical, arc cylindrical, or herringbone cylindrical.

6. The three dimensional mechanical ultrasound probe of claim 5, wherein the face gear is spur cylindrical and the cylindrical gear is spur cylindrical; or the face gear is helical cylindrical and the cylindrical gear is helical cylindrical.

7. The three dimensional mechanical ultrasound probe of claim 6, wherein the cylindrical gear is an involute gear.

8. The three dimensional mechanical ultrasound probe of claim 1, further comprising:

a probe base comprising a base and a side wall extending in a same direction from an end of the base, two ends of the transducer base being rotatably arranged on opposite side walls of the probe base;

wherein, the reduction gearbox is arranged at a side of the base away from the transducer base.

9. The three dimensional mechanical ultrasound probe of claim 8, wherein one end of the driving cylindrical gear shaft being rotatably connected to the probe base, the other end of the driving cylindrical gear shaft passing through the reduction gearbox and being connected with an output shaft of the driving motor.

10. The three dimensional mechanical ultrasound probe of claim 9, wherein an included angle formed between a rotating center line of the face gear and a rotating axis of the transducer base is equal to 0 degree;

a rotating axis of the cylindrical gear is perpendicular to the rotating center line of the face gear; and a rotating axis of the driving cylindrical gear is parallel to a rotating axis of the driven cylindrical gear.

11. The three dimensional mechanical ultrasound probe of claim 10, wherein the face gear is spur cylindrical, helical cylindrical, arc cylindrical, or herringbone cylindrical.

12. The three dimensional mechanical ultrasound probe of claim 11, wherein the face gear is spur cylindrical and the cylindrical gear is spur cylindrical; or the face gear is helical cylindrical and the cylindrical gear is helical cylindrical.

\* \* \* \* \*